United States Patent [19]
van der Merwe et al.

[11] Patent Number: 5,115,688
[45] Date of Patent: May 26, 1992

[54] DEVICE FOR SAMPLING MATERIAL FROM A MOVING BELT CONVEYOR

[75] Inventors: Eugene van der Merwe, Roodepoort; Ralph H. English, Johannesburg, both of South Africa

[73] Assignee: Johannesburg Consolidated Investment Company, South Africa

[21] Appl. No.: 475,351

[22] Filed: Feb. 5, 1990

[30] Foreign Application Priority Data

Feb. 8, 1989 [ZA] South Africa ............... 89/0962

[51] Int. Cl.⁵ ............................................. G01N 1/20
[52] U.S. Cl. ................................................. 73/863.91
[58] Field of Search ............ 73/863.91, 863.92, 864.31, 73/864.32

[56] References Cited

U.S. PATENT DOCUMENTS

| | | | |
|---|---|---|---|
| 3,181,369 | 5/1965 | Taylor | 73/863.91 |
| 4,611,498 | 9/1986 | Stahura | 73/863.91 X |
| 4,619,149 | 10/1986 | Long | 73/863.91 |
| 4,702,114 | 10/1987 | Cabonnes | 73/863.11 X |
| 4,790,196 | 12/1988 | Gould | 73/863.91 |
| 4,796,476 | 1/1989 | Long | 73/864.32 X |
| 4,884,462 | 12/1989 | Long | 73/863.91 |
| 4,919,000 | 4/1990 | Long | 73/863.91 |

FOREIGN PATENT DOCUMENTS

| | | | |
|---|---|---|---|
| 977578 | 11/1975 | Canada | 73/863.91 |
| 0165181 | 12/1985 | European Pat. Off. | |
| 0187443 | 7/1986 | European Pat. Off. | |
| 0373281 | 6/1990 | European Pat. Off. | |
| 2025908 | 12/1971 | Fed. Rep. of Germany | 73/863.91 |
| 874445 | 6/1987 | South Africa | |
| 628424 | 8/1978 | U.S.S.R. | 73/864.32 |
| 828007 | 5/1981 | U.S.S.R. | |
| 1281969 | 1/1987 | U.S.S.R. | 73/863.91 |

OTHER PUBLICATIONS

Derwent Publications, Ltd., *Soviet Inventions Illustrated*, Week E07, Jul. 31, 1982, (SU-828007).
Excerpts from "The Extractive Metallurgy of Gold in South Africa", (G. G. Stanley, editor, 1987), vol. 2, pp. 758-771.
Ramsey Engineering Company brochure dated (Jun. 1987), 4 pages.

*Primary Examiner*—Tom Noland
*Attorney, Agent, or Firm*—Eckert Seamans Cherin & Mellott

[57] ABSTRACT

A sampler for removing material, such as ore from a mining operation, from a moving belt conveyor includes a frame having a web and rod-like supports on which bristles are fixed, located between a pair of spaced blades arranged behind the blades' leading edges. A gearbox and electrical motor cooperate with the frame in order to periodically pass the frame across the moving belt in order to confine the material between the blades in a sampling zone which extends obliquely across the belt. The arrangement of the blades and the speed of the motor are designed to match the motion of the belt so that those portions of each blade passing across the belt follow substantially the same path as the respective leading edge thereof. Material confined in the sampling zone is displaced from the belt while the blades traverse the belt. The material displaced from the belt is conveniently reduced to a homogeneously state for assaying.

4 Claims, 3 Drawing Sheets

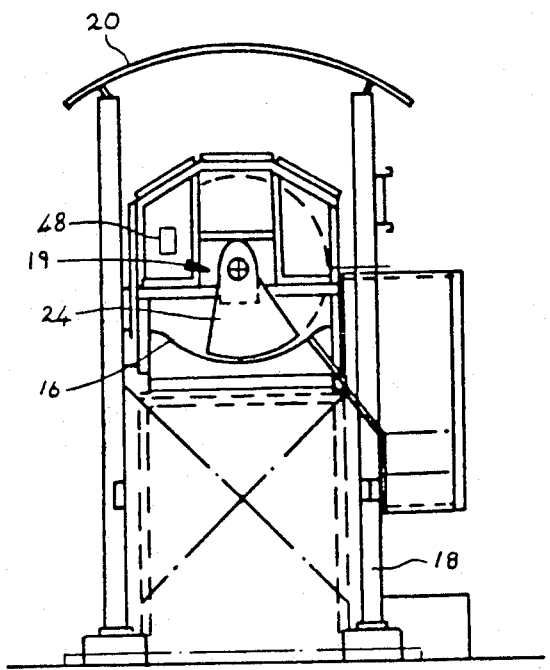
_Fig. 3_
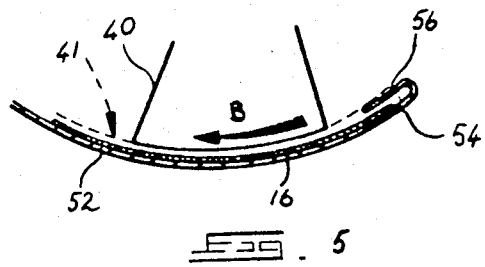
_Fig. 5_
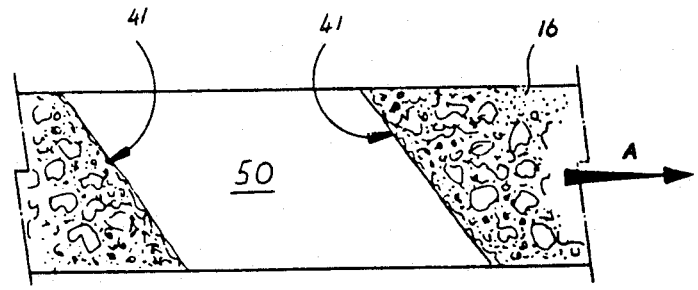
_Fig. 6_
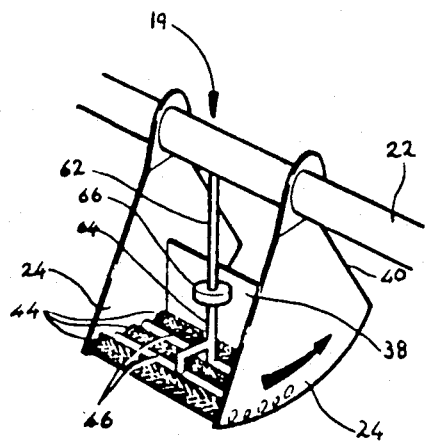
_Fig. 4_

DEVICE FOR SAMPLING MATERIAL FROM A MOVING BELT CONVEYOR

BACKGROUND OF THE INVENTION

This invention relates to a method and a device for sampling material from a moving belt conveyor. The material to be sampled may be the run-of-mine product of mines such as metal mines in which the mineral to be recovered is unevenly distributed in the ore removed from the mining area.

The run-of-mine product may be considered to be the product reaching the first stage of ore processing after leaving the mining area. Typically, in an underground gold or platinum mine, the run-of-mine product arrives at the surface through a shaft, having been blasted and screened underground.

The ore in such mines contains mineral values which are not consistent from one working area of the mine to the others. There is also inconsistency in the distribution of the mineral in ore taken from the same working area. In underground gold mines, for instance, the ore may be concentrated in relatively narrow reefs or seams surrounded by barren country rock. Some country rock is always removed in such cases together with the metal-bearing reef or seam, and its presence necessarily affects the grade of the ore processed.

It is highly desirable to sample the run-of-mine product for its mineral values in order to establish the efficiency of the extraction process.

Because of the large tonnages typically handled in metal mines, and the disruption to production which would occur by periodically stopping a moving conveyor to remove a representative sample, run-of-mine sampling has not successfully been carried out on metal mines in the past, as far as the applicant is aware.

Fully representative sampling of bulk products is possible where the product is homogeneous. For instance, in the processing of food products such as maize and flour, it is possible to extract a satisfactory sample at almost any point. The sample in such cases need not be large: only sufficient product need be removed to satisfy the needs of the sapling procedure itself.

Typically in such instances a sample can be scooped off a moving or stationary conveyor such as a belt conveyor to provide a fully representative sample of the product at that point in the plant and at that particular time.

It has been appreciated that in order to conduct proper sampling of the run-of-mine product on metal mines, it is necessary to take a portion of the entire stream of material passing through a particular point at a particular time. The run-of-mine product in such mines is often transported, at least at some stage, on belt conveyors. Hitherto, to conduct run-of-mine sampling, the conveyor has been stopped, a former placed over a portion of the belt, and the entire body of ore contained within the former has been removed. The removal has, at least in some instances, taken place by laborious manual methods. These procedures have been slow and somewhat erratic since the consistency of operation of the person voiding the former cannot readily be sustained. Since a substantial proportion of the metal is often found in fines which settle at the bottom of a troughed belt conveyor, any significant part of the fines left behind can destroy the accuracy of the sampling result.

The problem is rendered more complicated by the fact that the ores are often highly abrasive so that there is a good deal of wear on any but the most robust of equipment.

The problem resolves itself largely into one of repeatability. It is necessary to be able to undertake a consistently repeatable procedure and one which does not disturb, to any real extent, the continuity of flow of the ore into the processing plant.

If the conveyor from which the sample is to be taken is a conventional belt conveyor the problem is compounded by the fact that belt geometry varies from point to point along the length of the conveyor. The belt, generally of rubber, is supported on a series of rollers, arranged in sets along the conveyor frame. Each set is arranged in a trough configuration. Between each pair of adjacent roller sets the belt tends to trough in a longitudinal direction in addition to the troughing imposed transversely by the rollers, so that a mechanism which merely travels in a straight line across the belt to eject a portion of the ore on it would not provide a sufficiently complete body of material to be adequate for proper sampling. The material contained in the trough, both longitudinal and transverse, would not be removed, and its presence would distort the results of the assaying procedure carried out on the sample extracted.

It is not however necessary that every particle of the body of material removed from the stream of ore should be collected. Provided the sampling procedure is entirely consistent and the extent of removal of the ore from the conveyor is understood, together with the overall distribution of metal in the ore, a satisfactory sampling result can be achieved by importing the necessary bias into the assay results.

With these and related circumstances in mind, it is an object of the invention to provide a method and apparatus for sampling material from a moving belt conveyor, such as the run-of-mine products of metal mines and similar mines, so that a successful and consistent result can be achieved.

SUMMARY OF THE INVENTION

According to the invention a method of sampling material from a moving belt conveyor includes the steps of:

periodically passing a pair of spaced blades across the belt in order to confine material between the blades in a sampling zone extending obliquely across the belt; and displacing the material in the sampling zone from the belt while the blades traverse the belt.

The material is preferably displaced from the belt by sweeping the space located between the blades and behind their leading edges. Various forms of sweeping action, singly or in continuation, may be used.

The method may include the further step of troughing the belt transversely in relation to the direction of motion of the belt. Longitudinal troughing of the belt, however, is undesirable for the purpose of removing material from the belt. The above-mentioned method may hence include a further step of supporting the belt in a region beneath the sampling zone in order to keep the portion of the belt from which material is removed substantially straight in the longitudinal direction of the belt.

Material removed from the belt will generally be reduced to a homogeneous state, a portion of the homogeneous product then being assayed.

In a further aspect o the invention a sampler is provided for removing material from a moving belt conveyor, the sampler comprising:

a frame which includes a pair of spaced blades having leading edges, and sweeping means located between the blades and behind their leading edges; and drive means arranged to pass the frame periodically across t he belt so that the blades confine material between each other in a sampling zone which extends obliquely across the belt, while the sweeping means displaces the material so confined across the belt and off it.

The blades may conveniently comprise a pair of parallel plates.

The plates may be fixed on a shaft, with their planes obliquely inclined in relation to the shaft axis, which is preferably arranged parallel to the longitudinal axis of the belt conveyor.

The sweeping means may comprise or include a web which extends between the plates or sweeping the surface of the belt. Alternatively or in addition the sweeping means may include a set of bristles arranged between the plates. In order to assist the sweeping action the sampler ay further include means for agitating material in the sampling zone.

BRIEF DESCRIPTION OF THE DRAWINGS

FIG. 3 is a vertical section view along the line III—III of FIG. 1.

FIG. 4 is a perspective view of a frame and associated components of the sampler of FIGS. 1-3;

FIG. 5 is a semi-schematic cross-sectional view through the belt seen in preceding figures, with certain other components and features indicated;

FIG. 6 is a plan view of a portion of the belt of the preceding figures, showing the zone swept by the sampler of the invention.

DESCRIPTION OF A PREFERRED EMBODIMENT

Figure 1:
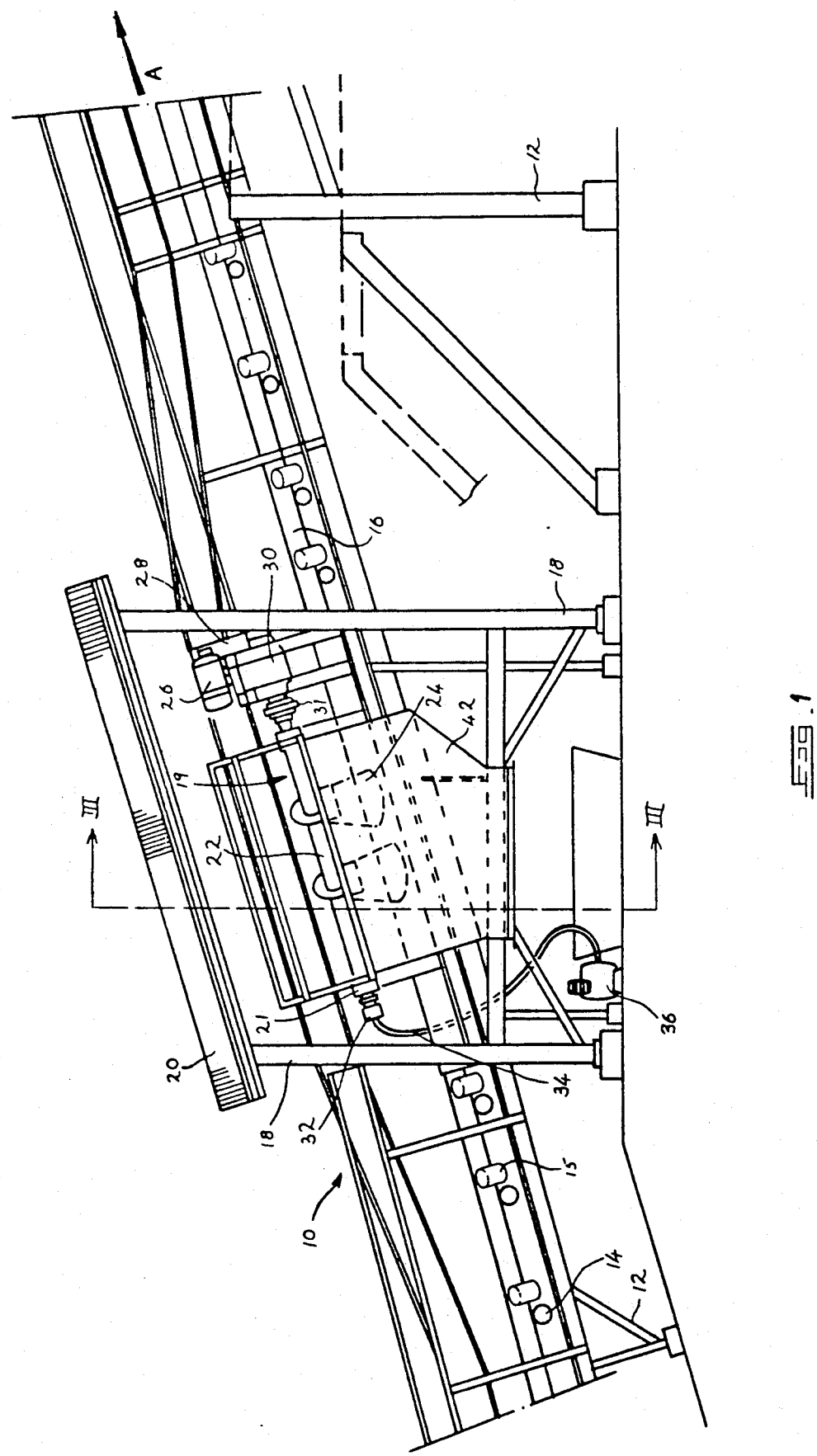
FIG. 1 is a simplified side elevation view of a portion of a belt conveyor for run-of-mine product at a metal mine equipped with a sampler of the invention.
Figure 2:
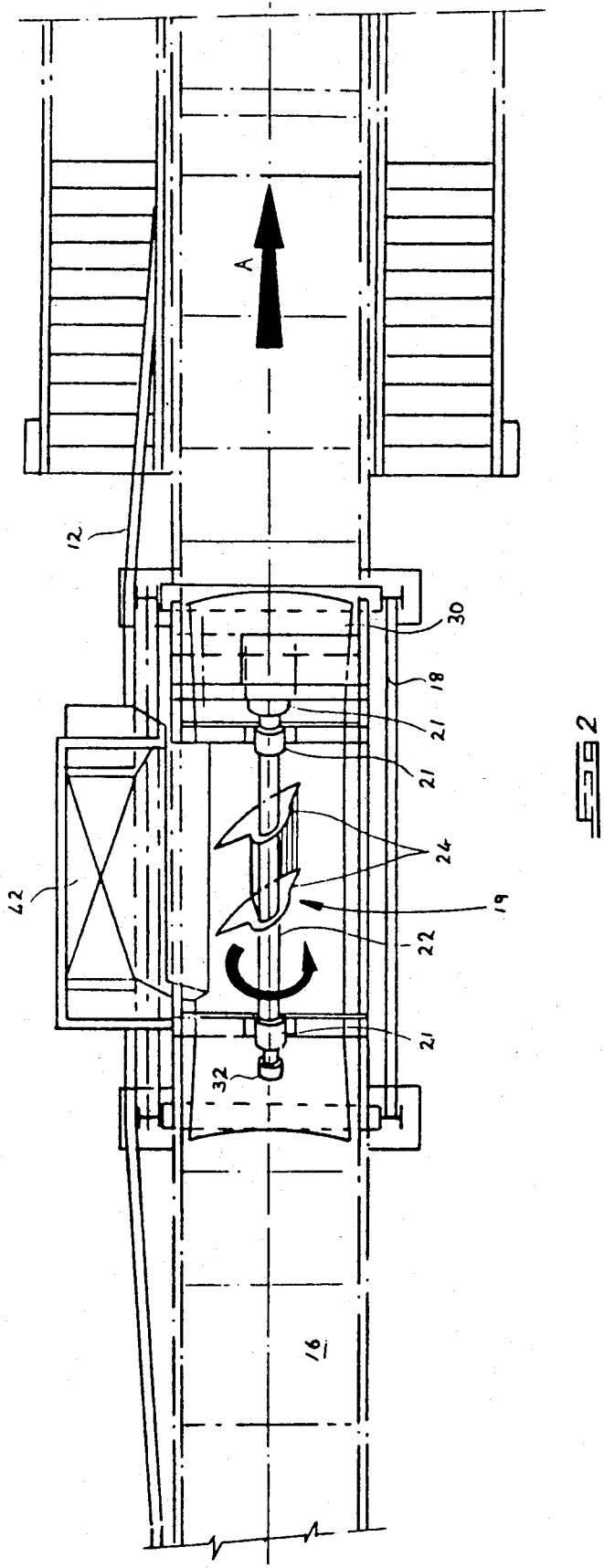
FIG. 2 is a plan view of the belt conveyor of FIG. 1, without its roof structure.

In the drawings, a mine belt conveyor 10 comprises a base 12 of a conventional type supporting series of sets of horizontal rollers 14 and inclined rollers 15 on which a rubber conveyor belt 16 is supported. The belt 16 is inclined to travel upward in the direction of the arrow A and t he belt carries run-of-mine ore arriving from underground up a mine shaft towards a processing plant (not illustrated).

A sampler of the invention is located below a roof structure 20 supported by a base 18 and covering a zone of the belt 16. Supported above the belt between pedestal bearings 21 is a sampler frame 19 comprising a tubular shaft 22 on which are fixed two plates 24 of paddle shape, spaced apart and parallel to each other. The axis of the shaft 22 is inclined at an angle of approximately 40° or more to the planes of the plates 24. This angle is dictated by several factors such as the linear speed of t he belt 16 and the rotational speed of the shaft 22, as appears more fully from the further description of the invention.

Drive means comprising an electrical motor 26 operating through V belts enclosed in a housing 28 transmits motion to a gearbox 30, which is connected via a coupling 31 to the shaft 22.

As appears from FIG. 1 the shaft 22 is arranged parallel to the direction of movement of the belt 16. The shaft 22 has at its lower end a fixed inlet cap 32 for receiving compressed air through a hose 34 that is connected to a source 36 of compressed air and directs this compressed air through a seal into the interior of the shaft 22.

The detailed construction of the sampler frame 19 is best seen in FIG. 4. It includes, between the plates 24, a rectangular web 38 located in a plane to which the axis of the shaft 22 is parallel. Each plate 24 has a leading edge 40 which, on rotation of the shaft 22, describes a locus 41 (FIG. 6) extending obliquely across the belt, with the web 38 between and behind the leading edges of the plates 24. The loci 41 define between t hem a sampling zone 50 extending obliquely across the belt 16, as illustrated in FIG. 6. The web 38, which extends to the radially outer edges of the plates 24, sweeps the surface of the belt 16 and displaces ore situated in the sampling zone 50 of the belt on rotation of the shaft 22, depositing this material in a chute 42 (FIG. 1) located on one side of the sampler frame 18.

Adjacent to the web 38 is a series of rod-like supports on which bristles 44 are fixed. Between each line of the bristles 44 is a rigid tube 46 which is perforated along its length. The holes in the tubes 46 are downwardly directed so that compressed air which they emit impinges on the belt 16 and agitates material on it. The bristles 44 enhance the sweeping action of the sampler which is further enhanced by the draughts of air provided through the tube 46.

The sampler is arranged, through a conventional timer mechanism schematically shown at 48 in FIG. 3, to cause the shaft 22 to undergo periodically a complete revolution at predetermined time intervals. These intervals will be determined by several factors, including the nature and quantity of material on the belt and the speed of movement of the belt. A typical belt speed is one meter per second and a typical frequency of sampling is once every 15 minutes.

The angle at which the plates 24 are arranged in relation to the axis of the shaft 22 is important. More particularly the loci 41 on the belt 16 described by the leading edges 40 should be followed as nearly as possible by the radial edges of the plates 24.

It is important to arrange the sampler frame 19 so that, in relation to the belt 16, it traverses the belt 16 at an oblique angle as shown in FIG. 6. The speed of the motor 26 is so co-ordinated with the motion of the belt 16 that, when the shaft 22 rotates, the ore on the belt is confined between the plates 24 and does not tend to accumulate against the aft plate 24, nor does the sampler tend to overtake material on the belt 16.

The material on the zone 50 of the belt is cleanly swept by the sampler into the chute 42, without disturbing to any significant extent the ore to either side of that zone 50.

It has been found that the combined action of the plates 24, web 38, bristles 44, and compressed air tubes 46 is to sweep the belt 16 virtually entirely of the material in the zone 50 traversed by t he sampler as the belt proceeds up the conveyor 10.

The belt 16 is conventionally troughed in a transverse direction, as shown in FIGS. 3 and 5, in view of its support on the inclined sets of rollers 15. The belt has a natural tendency to trough in the longitudinal direction too between each set of rollers 14 spaced along the length of the base 12, the longitudinal trough is unacceptable for the purposes of the invention, and for this reason a curved plate 52 (FIG. 5) is fixed to the conveyor base 18 in the zone of the sampler. The plate 52 bears against the lower surface of the belt 16 and keeps it longitudinally supported while permitting the required transverse troughing in the sampling zone.

In FIG. 5 it will also be seen that, at the edge 54 of the belt 16 first approached by the plates 24 of the sampler frame 19 as the shaft 22 rotates, a guard 56 is provided. This consists of a curved strip of steel, fixed to the plate 52, so that it extends over the edge 54 of the belt and prevents this edge from lifting. (Such lifting could of course lead to obstruction of the plates 24 and web 38 as they first cross the edge 54 of the belt; potential damage to the belt 16 and sampler frame 19 is accordingly avoided.)

The locus of the lower edge of the plates 24 of the sampler is shown in FIGS. 5 by the line 41, and the direction of rotation of the sampler frame by the arrow "B".

In practice, for a conventional belt of 1050 mm width, it has been found adequate to provide a sampler frame 19 in which the distance between the plates 24 (measured along the axis of the shaft 22) is 600 mm. Steel plate of approximately 12 mm thickness is used for the plates 24 and web 38.

The compressed air reaching the agitator tubes 46 arrives through tubes 62, 64 connected to the interior of the shaft 22 and jointed by a union 66.

A feature of the invention is that the sampler removes from the belt 16 substantially all the ore in the zone 50. Naturally total removal of every particle in this zone 50 is not possible, but a consistently high degree of removal has been found possible by the method and apparatus of the invention. To the extent that any material regularly remains on the belt 16 in the zone 50, a bias is present which can be statistically catered for when calculating the results of assaying.

Material entering the chute 42 on each occasion of sampling s collected and crushed to a suitable consistency. This mixes the material so that it becomes a product in which the metal values are homogeneously distributed through the sample. A portion of the sample which is statistically adequate for the purpose is then removed from the sample and assayed by conventional techniques to determine its mineral content. As noted above, the raw assay result can be adjusted to take account of any bias known to exist in the system, for instance to represent the known value of material consistently left behind on the belt 16 in the zone 50.

A sampler as described above has the necessary robustness to be reliable over a long period. This is essential for accurate sampling.

Various alternative constructions are of course possible. For instance, blades of a different form from the plates 24 might be provided to lead the sampler frame into and through the material on the belt and confine this material within the sampling zone.

In some embodiments the axis of the shaft 22 may not be parallel to the direction of movement of the belt 16. In this case the angle of obliquity of the plates 24 to the shaft 22 will differ from that in the embodiment illustrated, and may even be a zero degree.

We claim:

1. A method of sampling material from a moving troughed belt conveyor having a belt by means of a frame including a pair of spaced blades connected in oblique relationship to a shaft arranged above the belt and having a centered longitudinal axis thereof extending in parallel relationship to the direction of motion of the belt, the sampling method comprising the steps of:
   supporting the belt in a region beneath a sampling zone to keep said region of t he belt substantially straight in said direction of motion of the belt so that the belt does not trough in the direction of motion of the belt between spaced rollers for moving the belt;
   periodically rotating the shaft about said longitudinal axis at a predetermined speed so that portions of said blades passing across said region of the belt travel in substantially the same path as the respective leading edges thereof, thereby confining material between the blades in a sampling zone extending obliquely across the belt; and
   displacing the material in the sampling zone from the belt while the blades traverse the belt.

2. A method according to claim 1 which includes the further steps of reducing the material removed from the sampling zone to a homogeneous state and assaying a portion of the homogeneous product.

3. A sampler for removing material from a moving belt conveyor, comprising:
   a frame which includes a pair of spaced blades having leading edges, and a set of bristles arranged between the blades and behind the leading edges thereof to sweep a surface of a belt of said conveyor; and
   drive means arranged to pass the frame periodically across the belt so that the blades confine material between each other in a sampling zone which extends obliquely across the belt, said bristles displacing the material across the belt and off the belt.

4. A sampler for removing material from a moving belt conveyor, comprising:
   a frame which includes a pair of spaced blades having leading edges, and sweeping means including means to agitate material locating between the blades and behind leading edges thereof; and
   drive means arranged to pass the frame periodically across the belt so that the blades confine material between each other in a sampling zone which extends obliquely across the belt, said sweeping means simultaneously agitating and displacing the material across the belt and off said belt.

* * * * *

UNITED STATES PATENT AND TRADEMARK OFFICE
CERTIFICATE OF CORRECTION

PATENT NO. : 5,115,688
DATED : May 26, 1992
INVENTOR(S) : Eugene van der Merwe et al.

It is certified that error appears in the above-identified patent and that said Letters Patent is hereby corrected as shown below:

```
Column 1, line 44, replace "sapling" with --sampling--.
Column 3, line 1, replace "o" with --of--.
          line 8, replace "t he" with --the--.
          line 24, replace "ay" with --may--.
          line 48, after "supporting" insert --a--.
          line 52, replace "t he" with --the--.
          line 63, after "of" delete "t".
          line 64, replace "he" with --the--.
Column 4, line 62, replace "t he" with --the--.
          line 68, delete "too".
Column 5, line 1, after "12" replace "the" with --The--.
          line 20, replace "FIGS." with --FIG.--.
          line 43, after "sampling" replace "s" with --is--.
Column 6, line 17, replace "t he" with --the--.
```

Signed and Sealed this

Twenty-eighth Day of September, 1993

*Attest:*

BRUCE LEHMAN

*Attesting Officer*      *Commissioner of Patents and Trademarks*